US011807599B2

(12) United States Patent
Fischer et al.

(10) Patent No.: US 11,807,599 B2
(45) Date of Patent: Nov. 7, 2023

(54) ORGANIC CARBONATE PRODUCTION PROCESS

(71) Applicant: SHELL OIL COMPANY, Houston, TX (US)

(72) Inventors: Kai Jürgen Fischer, Amsterdam (NL); Evert Van Der Heide, Amsterdam (NL); Peter Van De Haar, Assen (NL); Udeogu Chijioke Onwusogh, Doha (QA); Nicoleta Cristina Nenu, Amsterdam (NL)

(73) Assignee: SHELL USA, INC., Houston, TX (US)

( * ) Notice: Subject to any disclaimer, the term of this patent is extended or adjusted under 35 U.S.C. 154(b) by 52 days.

(21) Appl. No.: 17/637,205

(22) PCT Filed: Aug. 6, 2020

(86) PCT No.: PCT/EP2020/072124
§ 371 (c)(1),
(2) Date: Feb. 22, 2022

(87) PCT Pub. No.: WO2021/037516
PCT Pub. Date: Mar. 4, 2021

(65) Prior Publication Data
US 2022/0281799 A1  Sep. 8, 2022

(30) Foreign Application Priority Data

Aug. 30, 2019 (EP) ..................... 19194630

(51) Int. Cl.
*C07C 68/04* (2006.01)
*B01D 3/00* (2006.01)
*B01D 3/14* (2006.01)
*B01J 31/10* (2006.01)
*C07C 68/08* (2006.01)

(52) U.S. Cl.
CPC .............. *C07C 68/04* (2013.01); *B01D 3/009* (2013.01); *B01D 3/143* (2013.01); *B01J 31/10* (2013.01); *C07C 68/08* (2013.01)

(58) Field of Classification Search
CPC .......... C07C 68/04; C07C 68/08; B01D 3/143
See application file for complete search history.

(56) References Cited

U.S. PATENT DOCUMENTS

| | | |
|---|---|---|
| 3,980,690 A | 9/1976 | Cipriani et al. |
| 5,491,524 A | 2/1996 | Hellmuth et al. |
| 5,550,278 A | 8/1996 | Rechner et al. |
| 5,648,529 A | 7/1997 | Jones et al. |
| 6,015,875 A | 1/2000 | Smith, Jr. et al. |
| 6,784,277 B2 | 8/2004 | Boden et al. |
| 7,153,432 B2 | 12/2006 | Kohler et al. |
| 7,160,524 B2 | 1/2007 | Lederer et al. |
| 9,346,727 B2 | 5/2016 | Hasse et al. |
| 9,403,693 B2 | 8/2016 | Locatelli et al. |
| 9,656,942 B2 | 5/2017 | Ii et al. |
| 10,590,009 B2 | 3/2020 | Fischer et al. |

FOREIGN PATENT DOCUMENTS

| | | |
|---|---|---|
| CN | 1067046 A | 12/1992 |
| CN | 101016245 A | 8/2007 |
| CN | 101198580 A | 6/2008 |
| CN | 101389587 A | 3/2009 |
| CN | 101597117 A | 12/2009 |
| CN | 101906196 A | 12/2010 |
| CN | 102814193 A | 12/2012 |
| CN | 103073429 A | 5/2013 |
| CN | 104892423 A | 9/2015 |
| CN | 107715857 A | 2/2018 |
| CN | 109534999 A | 3/2019 |
| JP | H0356134 A | 3/1991 |
| JP | 3975256 B2 | 9/2007 |
| JP | 2009242306 A | 10/2009 |
| JP | 4415108 B2 | 2/2010 |
| JP | 4714924 B2 | 7/2011 |
| KR | 101368349 B1 | 2/2014 |
| TW | 201100376 A | 1/2011 |
| WO | 2006109775 A1 | 10/2006 |

OTHER PUBLICATIONS

International Search Report and Written Opinion received for PCT Patent Application No. PCT/EP2020/072124, dated Nov. 2, 2020, 10 pages.
Tabanelli et al., "Conversion of Co2 to Valuable Chemicals: Organic Carbonate as Green Candidates for the Replacement of Noxious Reactants", Studies in Surface Science and Catalysis, vol. 178, Jan. 1, 2019, pp. 125-144, XP055671258.
Lnui et al., "Chemistry of Microporous Crystals", Studies in Surface Science and Catalysis, Proceedings of the International Symposium on Chemistry of Microporous Crystals, vol. 60, Jun. 26-29, 1990, pp. 3-384.
Pawar et al., "Understanding the synergy between MgO—CeO2 as an effective promoter and ionic liquids for high dimethyl carbonate production from CO2 and methanol", Chemical Engineering Journal, vol. 395, Sep. 1, 2020, 124970.
Ballivet-Tkatchenko et al., "Direct Synthesis of Dimethyl Carbonate With Supercritical Carbon Dioxide: Characterization of a Key Organotin Oxide Intermediate", Catalysis Today, vol. 115, Issue No. 1-4, Jun. 30, 2006, pp. 80-87.
Merza et al., "The Synthesis of Dimethyl Carbonate by The Oxicarbonylation of Methanol Over Cu Supported on Carbon Norit", Catalysis Letters, vol. 145, 2015, pp. 881-892.
Tomishige et al., "Catalytic Function of Ceo2 in Non-reductive Conversion of Co2 With Alcohols", Materials Today Sustainability, vol. 9, Sep. 2020, 100035.
Daniel et al., "Discovery of Very Active Catalysts for Methanol Carboxylation Into Dmc by Screening of a Large and Diverse Catalyst Library", New Journal of Chemistry, 2020, vol. 44 (16), pp. 6312-6320.

(Continued)

*Primary Examiner* — Kamal A Saeed
(74) *Attorney, Agent, or Firm* — SHELL USA, INC.

(57) ABSTRACT

The present invention relates to a process for preparing an organic carbonate, comprising contacting carbon dioxide with an alcohol in the presence of water and a catalyst in a reaction zone resulting in the production of the organic carbonate, wherein the organic carbonate is continuously removed from the reaction zone.

10 Claims, 1 Drawing Sheet

(56) References Cited

OTHER PUBLICATIONS

Sun et al., "Study of Thermodynamics and Experiment On Direct Synthesis of Dimethyl Carbonate From Carbon Dioxide And Methanol Over Yttrium Oxide", Industrial and Engineering Chemistry Research, vol. 59(10), 2020, pp. 4281-4290.

Arbeláez et al., "Transformation of Carbon Dioxide Into Linear Carbonates and Methane Over Cu-ni and Ru-fe Supported on Pellets Activated Carbon", Chemical Engineering Transactions, vol. 79, 2020, pp. 109-114.

Challa et al., "Coupling of Ch3oh and Co2 With 2-cyanopyridine for Enhanced Yields of Dimethyl Carbonate Over Zno-ceo2 Catalyst", Journal of Chemical Sciences, vol. 131(8), 2019, p. 86.

Pawar et al., "Greener Synthesis of Dimethyl Carbonate From Carbon Dioxide and Methanol Using a Tunable Ionic Liquid Catalyst", Open Chemistry, vol. 17(1), pp. 1252-1265.

Li et al., "Incorporation of Co2 into Carbonates Through Carboxylation/hydration Reaction", Greenhouse Gases-Science and Technology, vol. 8, Issue No. 5, 2018, pp. 803-838.

Giram et al., "Direct Synthesis of Diethyl Carbonate from Ethanol and Carbon Dioxide over Ceria Catalysts", New Journal of Chemistry, vol. 42, Issue No. 21, Sep. 17, 2018, pp. 17546-17552.

Aresta et al., "Energy Issues in the Utilization of Co2 in the Synthesis of Chemicals: the Case of the Direct Carboxylation of Alcohols to Dialkyl-carbonates", Catalysis Today, vol. 281, Mar. 1, 2017, pp. 345-351.

Zou et al., "Halogen-free Processes for Organic Carbonate Synthesis from Co2", Current Opinion in Green and Sustainable Chemistry, vol. 3, Feb. 2017, pp. 11-16.

Lang et al., "Green Catalytic Process for Cyclic Carbonate Synthesis from Carbon Dioxide under Mild Conditions", Chemical Record, vol. 16, Issue No. 3, 2016, pp. 1337-1352.

Nakagawa et al., "Direct Synthesis of Organic Carbonates from CO2 and Alcohols using Heterogeneous Oxide Catalysts", Green Carbon Dioxide: Advances in CO2 Utilization, vol. 9781118590881, 2014, pp. 119-148.

Dibenedetto et al., "Direct Carboxylation of Alcohols to Organic Carbonates: Comparison of the Group 5 Element Alkoxides Catalytic Activity: an Insight Into the Reaction Mechanism and Its Key Steps", Catalysis Today, vol. 115, Issue No. 1-4, Jun. 30, 2006, pp. 88-94.

Aresta et al., "An Integrated Approach to the Synthesis of Organic Carbonates: Discovery of New Catalysts", ACS Division of Fuel Chemistry, vol. 49, Issue No. 1, Jan. 1, 2004, 2 Pages.

Aresta et al., "Reaction Mechanisms in the Direct Carboxylation of Alcohols for the Synthesis of Acyclic Carbonates", Topics in Catalysis, vol. 58, Issue No. 1, 2015, pp. 2-14.

International Search Report and Written Opinion received for PCT Patent Application No. PCT/EP2016/064525, dated Aug. 17, 2016, 10 pages.

Aresta et al., "Integrated Approach to the Synthesis of Organic Carbonates: Discovery of New Catalysts", ACS National Meeting Book of Abstracts, vol. 227, Issue No. 1, p. 156. (Only English Abstract).

Kang, "Simulation of the Direct Synthesis of DMC from Methanol and CO2 Intensified by Reactive Distillation with Side Reactor", Engineering Science and Technology I Series, Aug. 15, 2016, Issue No. 8, 68 Pages.

Office Action Received for Chinese Application No. 202080059706.9, dated Jul. 4, 2023, 24 Pages(13 Pages of English Translation and 11 Pages of Official Copy).

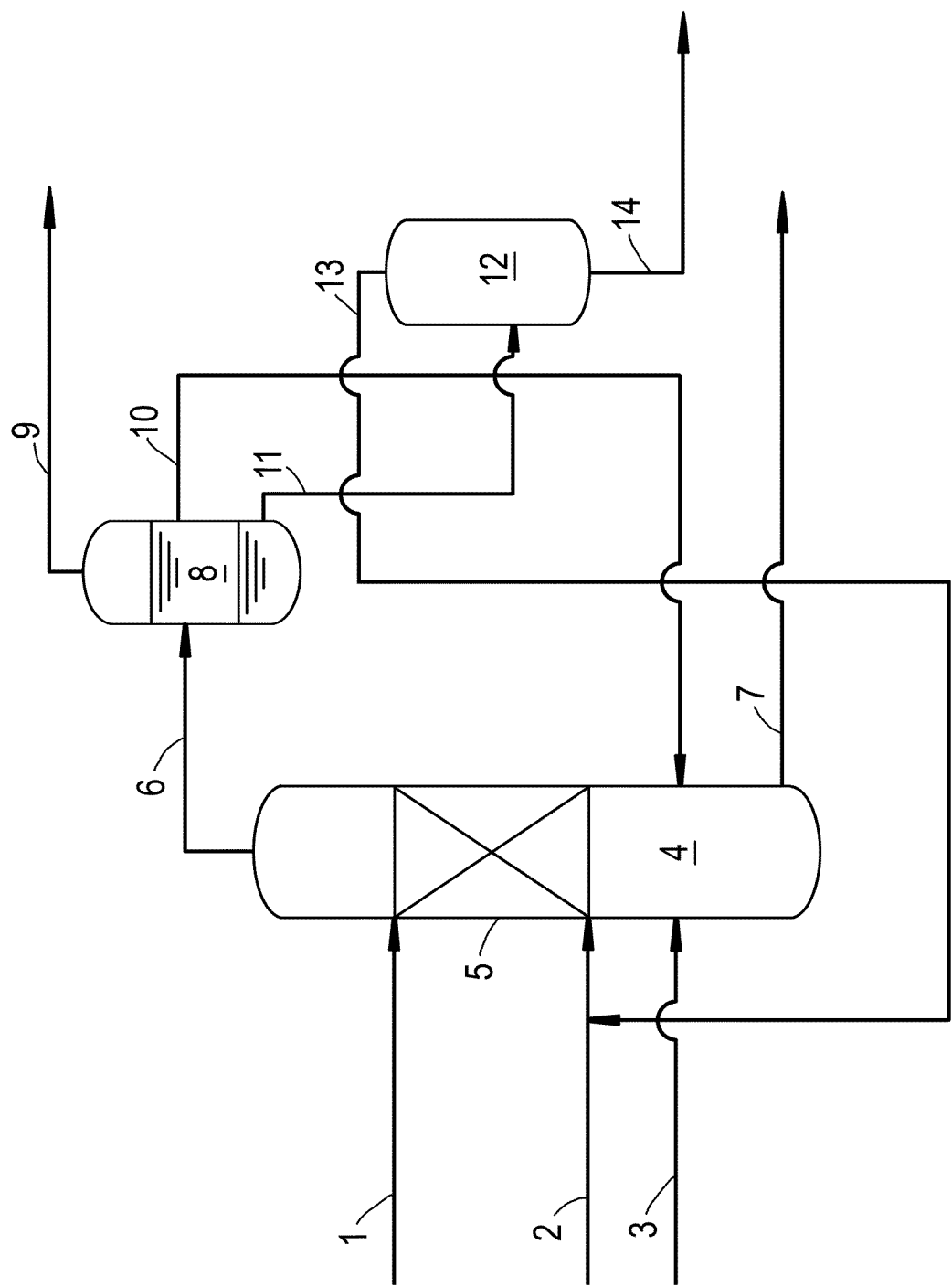

ORGANIC CARBONATE PRODUCTION PROCESS

CROSS REFERENCE TO RELATED APPLICATIONS

This is a National stage application of International application No. PCT/EP2020/072124, filed Aug. 6, 2020, which claims priority of EP application No. 19194630.0, filed 30 Aug. 2019 which is incorporated herein by reference in its entirety.

FIELD OF THE INVENTION

The present invention relates to a process for preparing an organic carbonate.

BACKGROUND OF THE INVENTION

Organic carbonates, such as dialkyl carbonates, diaryl carbonates and alkylene carbonates, find wide application in chemical industry. Organic carbonates are becoming widely used as solvents due to their low toxicity, as monomers for the preparation of polymers, and several other uses. The use of carbonates as monomers to form polymers may expand causing a large increase of their demand on the world market. Organic carbonates are important precursors for polycarbonate, polyester, polyurethane and polyamide production. Further, organic carbonates may be used as fuel oxygenate additives or solvents or entrainers or high permittivity components for lithium batteries or intermediates for chemical alcohol purification or medical or cosmetics use.

As the current and conventional synthetic technology is characterized by using phosgene as a building block, that is banned in several countries, development of new synthetic methodologies for organic carbonates is receiving much attention worldwide. The phosgene-free synthesis of organic carbonates, such as dimethyl carbonate (DMC) and diethyl carbonate (DEC), is attracting much attention. There is an ongoing need to develop improved organic carbonate production processes. It is an object of the present invention to provide an organic carbonate production process, which is technically advantageous, efficient and affordable.

SUMMARY OF THE INVENTION

Surprisingly it was found that the above-mentioned organic carbonate production process can be provided as a process wherein carbon dioxide is contacted with an alcohol in the presence of water and a catalyst in a reaction zone resulting in the production of the organic carbonate, and wherein the organic carbonate is continuously removed from the reaction zone.

Accordingly, the present invention relates to a process for preparing an organic carbonate, comprising contacting carbon dioxide with an alcohol in the presence of water and a catalyst in a reaction zone resulting in the production of the organic carbonate, wherein the organic carbonate is continuously removed from the reaction zone.

It is known to produce organic carbonates from reacting an alcohol with carbon dioxide in the presence of a catalyst thereby producing the organic carbonate and water. A literature overview of this reaction type is provided in Section 3.2 of Chapter 7, titled "Conversion of $CO_2$ to Valuable Chemicals: Organic Carbonate as Green Candidates for the Replacement of Noxious Reactants" by T. Tabanelli et al., in "Studies in Surface Science and Catalysis", volume 178, 2019, Elsevier B. V. In said overview, it is recognized that the $CO_2$ direct condensation reaction with alcohols and diols suffers from several bottlenecks associated with an unfavourable thermodynamic equilibrium for said reaction. In said overview, it is mentioned that the continuous removal of water from the reaction medium would shift the unfavorable equilibrium towards the products. The solution according to said overview, is the use of an effective dehydrating agent. However, the continuous removal of the organic carbonate product as required in the present invention, is not disclosed or suggested in said overview.

BRIEF DESCRIPTION OF THE DRAWINGS

FIG. 1 illustrates an embodiment of the present invention.

DETAILED DESCRIPTION OF THE INVENTION

While the process of the present invention and streams or compositions used in said process may be described in terms of "comprising", "containing" or "including" one or more various described steps and components, respectively, they can also "consist essentially of" or "consist of" said one or more various described steps and components, respectively.

In the context of the present invention, in a case where a stream or composition comprises two or more components, these components are to be selected in an overall amount not to exceed 100%.

Further, where upper and lower limits are quoted for a property then a range of values defined by a combination of any of the upper limits with any of the lower limits is also implied.

In the examples and illustrations below, the locations of the different feed streams to and product streams from the distillation columns are selected such that the components are directed to where they are required by their relative volatilities. This means that different alcohol reactants and different organic carbonate products can result in different feed locations in order to drive the chemical and separation processes.

In the present invention, carbon dioxide is contacted with an alcohol in the presence of water and a catalyst in a reaction zone, thereby producing an organic carbonate. The overall reaction is illustrated below with reference to dimethyl carbonate as the targeted organic carbonate:

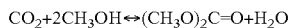

$$CO_2 + 2CH_3OH \leftrightarrow (CH_3O)_2C=O + H_2O$$

Such carboxylation of alcohols has limitations due to the thermodynamics. It has an unfavorable equilibrium towards the products organic carbonate and water. However, since in the present invention the organic carbonate is continuously removed from the reaction zone, the thermodynamic equilibrium is shifted advantageously towards the products. In addition, in the present invention, water should be present in addition to a catalyst, which water may be fed as further described below. Therefore, in the present invention no dehydrating agents, such as molecular sieves or sodium or magnesium sulfate, are used as in the above-mentioned literature overview.

Furthermore, advantageously, the present invention enables the direct synthesis of organic carbonates starting from carbon dioxide (taken for example from flue gas) and for example (bio)ethanol that could originate from fermentation and alcohol feed streams that normally contain water. As water is needed in the present invention any way, advantageously, said water does not have to be separated from the alcohol before use in the present invention.

Thus, in the present invention, the organic carbonate is continuously removed from the reaction zone. The present process is preferably a continuous process. Preferably, such continuous removal of the organic carbonate is achieved by performing the reaction in a distillation column. Within the present specification, a "distillation column" refers to a column wherein distillation is performed, said distillation being a process of separating the components from a liquid mixture of components by using selective boiling and condensation, wherein part of the condensed liquid may or may not be recycled (reflux) to the column.

In this way, advantageously, the production and separation of the organic carbonate is carried out simultaneously in a distillation column, thereby also shifting the thermodynamic equilibrium towards the products resulting in the production of more organic carbonate. Thus, it is preferred that the reaction zone is part of a distillation column and the organic carbonate is continuously removed from the distillation column. Such distillation column is also referred to as a "reactive distillation column".

In the present invention, it is preferred that carbon dioxide, the alcohol and water are fed to the reaction zone. They may be fed separately and/or together. For example, the alcohol and water may be fed together to the reaction zone. The amount of water fed to the reaction zone, based on the total amount of water and alcohol fed to the reaction zone, may be of from 1 to 99 wt. %, preferably 5 to 95 wt. %, more preferably 10 to 80 wt. %, most preferably 20 to 50 wt. %. The presence of water in the present process may have a variety of advantages. Firstly, water is a suitable polar reaction medium for the intended reaction wherein carbon dioxide may be dissolved, as further described below. Secondly, water may be helpful in any further purification of a stream comprising carbon dioxide, water, alcohol and organic carbonate, as further described below. Thirdly, water may be needed to activate and stabilize a catalyst used in the present process, as further described below.

It is preferred that carbon dioxide is fed to the reaction zone in such amount that the aqueous liquid phase present in the reaction zone is saturated with dissolved carbon dioxide. Such dissolved carbon dioxide may also be referred to as "liquid" carbon dioxide.

In the present invention, it is preferred that carbon dioxide is contacted with an alcohol in the presence of water and a catalyst in a reaction zone of a first distillation column resulting in a mixture comprising carbon dioxide, water, alcohol and organic carbonate, wherein organic carbonate is continuously removed from the first distillation column in a bottom stream from the first distillation column and wherein the top stream from the first distillation column comprises carbon dioxide, water, alcohol and optionally organic carbonate. The organic carbonate may be present in said top stream because it may form an azeotrope with water. For example, it is known that dialkyl carbonates form an azeotrope with water, whereas alkylene carbonates do not. Thus, in case the organic carbonate is a dialkyl carbonate, it will end up in both the bottom stream and the top stream.

Within the present specification, by "top stream" or "bottom stream" from a column reference is made to a stream which exits the column at a position, which is between 0% and 30%, more suitably between 0% and 20%, even more suitably between 0% and 10%, based on the total column length, from the top of the column or the bottom of the column, respectively.

It is preferred that fresh water is fed to the first distillation column at a position which is above the position at which fresh alcohol is fed, preferably at a position which is at or above the top of the reaction zone. Further, it is preferred that fresh alcohol is fed to the first distillation column at a position which is below the position at which fresh water is fed, preferably at a position which is at or below the bottom of the reaction zone. Said reaction zone may be a zone within the first distillation column which comprises a packing containing a heterogeneous catalyst, for example a structured packing. By "fresh" water or alcohol reference is made to non-recycled water or alcohol. Alternatively or additionally, fresh water and fresh alcohol may be co-fed as part of an aqueous alcohol stream, preferably at a position which is at or below the bottom of the reaction zone. Still further, it is preferred that carbon dioxide is fed a position which is below the position at which fresh alcohol is fed. An inert gas, such as nitrogen, may be co-fed together with the carbon dioxide. Further, carbon dioxide may be co-fed together with water. Advantageously, water does not need to be removed from feed streams comprising both carbon dioxide and water as water is needed any way in the present process, inter alia for dissolving the carbon dioxide as described above. In the present invention, a stream comprising of from 5 to 100 wt. % of carbon dioxide, the balance comprising inert gas and/or water, may be fed.

In case the above-mentioned top stream from the first distillation column comprises carbon dioxide, water, alcohol and organic carbonate, it is preferred that said top stream is at least partially condensed and separated into a gas stream comprising carbon dioxide, a first liquid stream comprising organic carbonate and alcohol and a second liquid stream comprising alcohol and water. The latter separation may be performed by using a decanter. The separated stream comprising carbon dioxide may be removed from the process or recycled to the first distillation column. The separated stream comprising organic carbonate and alcohol may be recycled to the first distillation column so that further organic carbonate may be recovered and alcohol may be recycled to the reaction zone. It is preferred that said stream is fed to the first distillation column at a position which is below the bottom of the reaction zone and below the position at which fresh alcohol is fed. The separated stream comprising alcohol and water may be fed to a second distillation column wherein separation into a stream comprising alcohol and a stream comprising water is performed. The separated stream comprising alcohol from the second distillation column may be recycled to the first distillation column. Said stream may be fed separately or co-fed together with fresh alcohol to the first distillation column. The separated stream comprising water from the second distillation column may be removed from the process.

Preferably, the temperature in the reaction zone is of from 50 to 200° C., more preferably 60 to 160° C., most preferably 70 to 140° C. Further, preferably, the pressure in the reaction zone is of from 5 mbar to 10 bar, more preferably 10 mbar to 5 bar. The pressure may be selected and set such that the desired boiling temperature in the reaction zone is realized.

In the present invention, the alcohol may be an aromatic $C_5$-$C_9$ alcohol and/or an aliphatic $C_1$-$C_{30}$ alcohol. The aromatic $C_5$-$C_9$ alcohol may be phenol. Preferably, in the present invention the alcohol is an aliphatic $C_1$-$C_{30}$ alcohol. Preferably, the aliphatic $C_1$-$C_{30}$ alcohol has 1 to 10 carbon atoms, more preferably 1 to 5 carbon atoms, most preferably 1 to 3 carbon atoms. Further, preferably, the aliphatic $C_1$-$C_{30}$ alcohol is selected from methanol, ethanol and isopropanol, more preferably methanol and ethanol, most preferably ethanol.

Further, in the present invention, the alcohol may contain one hydroxyl group (monohydric alcohol) or two or more hydroxyl groups (polyhydric alcohol). In case of a monohydric alcohol, a linear organic carbonate is formed which may be a dialkyl carbonate (in case the starting alcohol is aliphatic) or a diaryl carbonate (in case the starting alcohol is aromatic). In case of a polyhydric alcohol, two of the hydroxyl groups, especially two hydroxyl groups separated from each other by 2 or 3 carbon atoms, may react with carbon dioxide to form a cyclic organic carbonate. An example of such polyhydric alcohol is a monoalkylene glycol, for example monoethylene glycol or monopropylene glycol, which when reacted with carbon dioxide results in the formation of an alkylene carbonate, for example ethylene carbonate and propylene carbonate. Another example of such polyhydric alcohol is glycerol which when reacted with carbon dioxide results in the formation of a glycerol carbonate.

As mentioned above, in the present process, both an aromatic $C_5$-$C_9$ alcohol and an aliphatic $C_1$-$C_{30}$ alcohol may be fed. This has the advantage that alkyl aryl carbonates may be formed which may be disproportionated into a dialkyl carbonate and a diaryl carbonate. For example, in a case where in the present process a mixture of methanol and phenol is used, dimethyl carbonate and methyl phenyl carbonate may be formed. Disproportionation of the methyl phenyl carbonate would then result in diphenyl carbonate and further dimethyl carbonate.

In the present invention, a catalyst should be used. Any catalyst that catalyzes the formation of organic carbonate from carbon dioxide and alcohol may be used.

It is preferred that the catalyst is an acidic catalyst. Further, it may be preferred that the catalyst is a basic catalyst. Generally, a catalyst having both acidic and basic properties may be used. Thus, in the present invention, the catalyst may be acidic or basic or may have acidic and basic properties. Further, preferably, the catalyst is a heterogeneous catalyst. Further, preferably said heterogeneous catalyst is an immobilized catalyst, which implies that it cannot leave the reaction zone. Immobilization of a heterogeneous catalyst may for example be achieved by incorporating the catalyst in a packing in the reaction zone.

The above-mentioned acidic catalyst may be an acidic resin, in specific an acidic ion-exchange resin. Said acidic resin may be any acidic resin that can protonate water and/or alcohol as present in the present process. The proton of the acidic functionality of such acidic resin may advantageously activate the alcohol to undergo the desired reaction. In case such acidic resin is used, water as present in the present process may advantageously be used in both activating and stabilizing such acidic resin. For an acidic resin may swell substantially when in contact with water. If it becomes dry, the carrier polymer matrix may become brittle and any broken pieces may escape from the cage in which they are kept in the reaction zone with a packing. This implies both stabilizing and activating the catalytic acidic resin. Further, water also keeps pores of the resin open and the acidic functionality accessible.

A suitable example of an acidic resin is an acidic resin based on sulfonated polystyrene. The latter acidic resin contains sulfonic acid (—$SO_3H$) groups. Such acidic resin may be macoreticular (macroporous). Suitable, commercially available examples of acidic ion-exchange resins based on sulfonated polystyrene are Amberlyst 15 and Amberlyst 48.

Typically, a wide variety of catalysts may be used in the present invention. The nature of the catalyst is not essential for the present invention. For example, one or more of the catalysts as described in the below literature references [1] to [9] may be used in the present invention. The disclosures of said literature references are incorporated herein by reference.

MgO—$CeO_2$, as disclosed in ref [1], may be used as a catalyst in the present invention.

An organo-tin material, for example n-$Bu_2Sn(OCH_3)_2$, as disclosed in ref [2], may be used as a catalyst in the present invention.

An organo-copper material, for example Cu-AC [AC=active carbon], as disclosed in ref [3], may be used as a catalyst in the present invention.

$CeO_2$, as disclosed in ref [4], may be used as a catalyst in the present invention.

Ref [5] discloses the following. A large diversity of catalysts has already been tested for the direct synthesis of DMC (dimethyl carbonate), including organic metal-alkoxy compounds, metal oxides, metal-supported catalysts and ionic liquids. It is generally proposed that well-balanced acidic and basic properties play a key role in DMC synthesis for methanol activation. The majority of metal oxide studies deal with ceria or zirconia. The effects of crystal structure and morphology on activity are still under debate. Ceria catalysts exhibiting nanorods, nanocubes, octahedrons and spindle-like morphologies show different activities. Generally, the observed tendency is that mixed oxides often perform better than pure oxides. Hence, authors have explored modified ceria and zirconia such as $H_3PO_4$-functionalized $ZrO_2$, ceria doped with $Al_2O_3$, $Fe_2O_3$, as well as mixed oxides of ceria-zirconia. One or more of said catalysts, as disclosed in ref [5], may be used as a catalyst in the present invention. Said $CeO_2$ may be used in combination with one or more of Al, Zn, Fe, La, Y, Gd, Sm, Zr, Nd, Nb, Ti.

Yttrium oxide, $Y_2O_3$, as disclosed in ref [6], may be used as a catalyst in the present invention.

A metal/active carbon material, for example Cu—Ni/AC and Ru—Fe/AC [AC=active carbon], as disclosed in ref [7], may be used as a catalyst in the present invention.

Ref [8] discloses the following. ZnO—$CeO_2$ combined with 2-cyanopyridin can be used to remove the water formed during the reaction. The superior catalytic activity is a unified effect of crystalline size of $CeO_2$ and presence of an optimum number of acidic and basic sites. Said ZnO—$CeO_2$ catalyst, as disclosed in ref [8], may be used as a catalyst in the present invention.

Ref [9] discloses the following. Different types of catalysts have been reported in DMC synthesis such as: organotin, copper-based catalysts, homogeneous and heterogeneous catalysts, organometallic complexes, phosphines, organic bases, metal oxides, acid-base bifunctional systems, zeolite-smectite catalysts, and supported organic base catalysts. One or more of said catalysts, as disclosed in ref [9], may be used as a catalyst in the present invention.

LITERATURE REFERENCES [1] TO [9]

[1] Pawar et al., "Understanding the synergy between MgO—$CeO_2$ as an effective promoter and ionic liquids for high dimethyl carbonate production from $CO_2$ and methanol", 2020, Chemical Engineering Journal 395, 124970.

[2] Ballivet-Tkatchenko et al., "Direct synthesis of dimethyl carbonate with supercritical carbon dioxide: characterization of a key organotin oxide intermediate", Catal. Today., 115, 2006, pages 80-87.

[3] Merza et al., "The synthesis of dimethyl carbonate by the oxicarbonylation of methanol over Cu supported on carbon norit", Catal. Lett., 145, 2015, pages 881-892.

[4] Tomishige et al., "Catalytic function of $CeO_2$ in non-reductive conversion of $CO_2$ with alcohols", 2020, Materials Today Sustainability, 9, 100035.

[5] Daniel et al., "Discovery of very active catalysts for methanol carboxylation into DMC by screening of a large and diverse catalyst library", 2020, New Journal of Chemistry, 44(16), pages 6312-6320.

[6] Sun et al., "Study of thermodynamics and experiment on direct synthesis of dimethyl carbonate from carbon dioxide and methanol over yttrium oxide", 2020, Industrial and Engineering Chemistry Research, 59(10), pages 4281-4290.

[7] Arbeláez et al., "Transformation of carbon dioxide into linear carbonates and methane over Cu—Ni and Ru—Fe supported on pellets activated carbon", 2020, Chemical Engineering Transactions, 79, pages 109-114.

[8] Challa et al., "Coupling of $CH_3OH$ and $CO_2$ with 2-cyanopyridine for enhanced yields of dimethyl carbonate over ZnO—$CeO_2$ catalyst", 2019, Journal of Chemical Sciences 131(8), 86.

[9] Pawar et al., "Greener synthesis of dimethyl carbonate from carbon dioxide and methanol using a tunable ionic liquid catalyst", 2020, Open Chemistry, 17(1), pages 1252-1265.

The invention is further illustrated in FIG. 1.

In the process as shown in FIG. 1, a liquid feed stream (1) comprising water, a liquid feed stream (2) comprising ethanol and a gaseous feed stream (3) comprising carbon dioxide are sent to a reactive distillation column (4) at different positions, wherein water is fed at the highest position and carbon dioxide is fed at the lowest position, as indicated in FIG. 1. Reactive distillation column (4) contains a reaction zone (5) which contains a heterogeneous catalyst which can catalyze the formation of organic carbonate (e.g. diethyl carbonate) from carbon dioxide and alcohol (e.g. ethanol).

Bottom stream (7) from reactive distillation column (4) comprises the desired product, namely diethyl carbonate. Top stream (6) from reactive distillation column (4) comprises diethyl carbonate, water, ethanol and carbon dioxide and is sent through a partial condensation step to a decanter (8). Gaseous carbon dioxide is vented from decanter (8) via its top. In decanter (8), two liquid phases are separated, wherein the top phase comprising diethyl carbonate and ethanol is recycled in first liquid stream (10) to reactive distillation column (4) and the bottom phase comprising ethanol and water is sent in second liquid stream (11) to a distillation column (12). In distillation column (12), stream (11) is separated into a top stream (13) comprising ethanol which is recycled to reactive distillation column (4) by combining it with ethanol feed stream (2) and a bottom stream (14) comprising water which is removed from the process.

We claim:

1. A process for preparing an organic carbonate, comprising contacting carbon dioxide and an alcohol in the presence of water and a catalyst in a reaction zone resulting in the production of the organic carbonate, wherein the organic carbonate is continuously removed from the reaction zone, and wherein the reaction zone is part of a distillation column and the organic carbonate is continuously removed from the distillation column.

2. The process according to claim 1, wherein the alcohol is an aromatic $C_5$-$C_9$ alcohol and/or an aliphatic $C_1$-$C_{30}$ alcohol.

3. The process according to claim 1, wherein the temperature is of from 50 to 200° C.

4. The process according to claim 1, wherein the pressure is from 5 mbar to 10 bar.

5. The process according to claim 1, wherein carbon dioxide is contacted with an alcohol in the presence of water and a catalyst in a reaction zone of a first distillation column resulting in a mixture comprising carbon dioxide, water, alcohol and organic carbonate, wherein organic carbonate is continuously removed from the first distillation column in a bottom stream from the first distillation column and wherein the top stream from the first distillation column comprises carbon dioxide, water, alcohol and optionally organic carbonate.

6. The process according to claim 5, wherein the top stream from the first distillation column comprises carbon dioxide, water, alcohol and organic carbonate, and wherein:

said top stream is at least partially condensed and separated into a gas stream comprising carbon dioxide, a first liquid stream comprising organic carbonate and alcohol and a second liquid stream comprising alcohol and water;

the separated first liquid stream comprising organic carbonate and alcohol is recycled to the first distillation column;

the separated second liquid stream comprising alcohol and water is fed to a second distillation column wherein separation into a stream comprising alcohol and a stream comprising water is performed;

the separated stream comprising alcohol from the second distillation column is recycled to the first distillation column.

7. The process according to claim 1, wherein the catalyst is an acidic catalyst.

8. The process according to claim 7, wherein the acidic catalyst is an acidic resin.

9. The process according to claim 1, wherein the catalyst is a heterogeneous, immobilized catalyst.

10. The process according to claim 8, wherein the acidic catalyst is an acidic resin based on sulfonated polystyrene.

* * * * *